US012193727B2

United States Patent
Clark et al.

(10) Patent No.: US 12,193,727 B2
(45) Date of Patent: *Jan. 14, 2025

(54) DEVICES AND METHODS FOR ENHANCED DENERVATION PROCEDURES

(71) Applicant: Boston Scientific Scimed, Inc., Maple Grove, MN (US)

(72) Inventors: Bryan Allen Clark, Forest Lake, MN (US); Akshay Ashok Gupte, Minneapolis, MN (US); Bryce Calvin Beverlin, II, St. Paul, MN (US); David Ernest Wechter, San Francisco, CA (US); Kate Taylor, Minneapolis, MN (US)

(73) Assignees: Boston Scientific Scimed, Inc., Maple Grove, MN (US); Regents of the University of Minnesota, Minneapolis, MN (US)

( * ) Notice: Subject to any disclaimer, the term of this patent is extended or adjusted under 35 U.S.C. 154(b) by 14 days.

This patent is subject to a terminal disclaimer.

(21) Appl. No.: 18/072,005

(22) Filed: Nov. 30, 2022

(65) Prior Publication Data

US 2023/0100876 A1    Mar. 30, 2023

Related U.S. Application Data

(60) Continuation of application No. 16/863,823, filed on Apr. 30, 2020, now Pat. No. 11,540,874, which is a
(Continued)

(51) Int. Cl.
*A61B 18/14* (2006.01)
*A61B 18/00* (2006.01)
(Continued)

(52) U.S. Cl.
CPC ..... *A61B 18/1477* (2013.01); *A61M 39/0208* (2013.01); *A61B 2018/0022* (2013.01);
(Continued)

(58) Field of Classification Search
CPC ...... A61B 18/1477; A61B 2018/00434; A61B 2018/00577; A61B 2018/00964; A61M 39/0208
See application file for complete search history.

(56) References Cited

U.S. PATENT DOCUMENTS

| | | |
|---|---|---|
| 2,459,325 A | 1/1949 | Knowles |
| 3,134,861 A | 5/1964 | Dempsey et al. |

(Continued)

FOREIGN PATENT DOCUMENTS

| | | |
|---|---|---|
| CN | 102198015 | 9/2011 |
| CN | 203815580 | 9/2014 |

(Continued)

OTHER PUBLICATIONS

"Disposable RF Injection Electrodes," Cosman Medical, Inc., https://www.cosmanmedical.com/wp-content/uploads/2014/03/COSMAN-Disposable-Injection-RF-Electrodes-and-Needles-CR-CP-CN.pdf, Mar. 2014 (2 pages).

(Continued)

*Primary Examiner* — Bradley J Osinski
(74) *Attorney, Agent, or Firm* — Pauly, DeVries Smith & Deffner LLC

(57) ABSTRACT

The present disclosure relates to methods, devices, kits and systems for enhancing the efficacy and longevity of denervation procedures.

11 Claims, 3 Drawing Sheets

Related U.S. Application Data division of application No. 15/357,795, filed on Nov. 21, 2016, now Pat. No. 10,675,085.

(60) Provisional application No. 62/258,986, filed on Nov. 23, 2015.

(51) Int. Cl.
  *A61M 25/10* (2013.01)
  *A61M 39/02* (2006.01)

(52) U.S. Cl.
  CPC ............ *A61B 2018/00285* (2013.01); *A61B 2018/00434* (2013.01); *A61B 2018/00577* (2013.01); *A61B 2018/00964* (2013.01); *A61B 2218/007* (2013.01); *A61M 2025/105* (2013.01)

(56) References Cited

U.S. PATENT DOCUMENTS

| | | | |
|---|---|---|---|
| 5,697,927 | A | 12/1997 | Imran et al. |
| 7,291,146 | B2 | 11/2007 | Koenig et al. |
| 7,306,596 | B2 | 12/2007 | Hillier et al. |
| 7,416,549 | B2 | 8/2008 | Young et al. |
| 7,742,795 | B2 | 6/2010 | Stone et al. |
| 7,822,215 | B2 | 10/2010 | Carazo et al. |
| 7,918,852 | B2 | 4/2011 | Tullis et al. |
| 7,945,331 | B2 | 5/2011 | Vilims |
| 8,052,679 | B2 | 11/2011 | Young |
| 8,100,896 | B2 | 1/2012 | Podhajsky |
| 8,504,147 | B2 | 8/2013 | Deem et al. |
| 8,548,600 | B2 | 10/2013 | Deem et al. |
| 8,774,937 | B2 | 7/2014 | Mercanzini et al. |
| 8,788,042 | B2 | 7/2014 | Mercanzini et al. |
| 8,788,064 | B2 | 7/2014 | Mercanzini et al. |
| 8,882,764 | B2 | 11/2014 | Sutton et al. |
| 8,939,969 | B2 | 1/2015 | Temelli et al. |
| 8,989,859 | B2 | 3/2015 | Deem et al. |
| 9,002,460 | B2 | 4/2015 | Parker |
| 9,037,259 | B2 | 5/2015 | Mathur |
| 9,072,906 | B2 | 7/2015 | Mercanzini et al. |
| 9,125,667 | B2 | 9/2015 | Stone et al. |
| 9,149,329 | B2 | 10/2015 | Azamian et al. |
| 9,277,955 | B2 | 3/2016 | Herscher et al. |
| 10,194,980 | B1 | 2/2019 | Brar et al. |
| 10,675,085 | B2 | 6/2020 | Clark et al. |
| 11,540,874 | B2 | 1/2023 | Clark, Jr. et al. |
| 2002/0042597 | A1 | 4/2002 | Hartlaub |
| 2003/0181959 | A1 | 9/2003 | Dobak |
| 2004/0047807 | A1* | 3/2004 | Meyer .................. A61K 31/407 424/9.42 |
| 2007/0012507 | A1 | 1/2007 | Lyon |
| 2007/0016185 | A1 | 1/2007 | Tullis et al. |
| 2007/0135875 | A1* | 6/2007 | Demarais ................ A61N 1/28 607/96 |
| 2008/0188912 | A1 | 8/2008 | Stone et al. |
| 2011/0004087 | A1 | 1/2011 | Fish et al. |
| 2011/0160723 | A1 | 6/2011 | Tullis et al. |
| 2012/0095461 | A1 | 4/2012 | Herscher et al. |
| 2012/0259269 | A1 | 10/2012 | Meyer |
| 2013/0089229 | A1 | 4/2013 | Kristo et al. |
| 2013/0096549 | A1 | 4/2013 | Organ et al. |
| 2013/0165916 | A1 | 6/2013 | Mathur et al. |
| 2014/0018880 | A1 | 1/2014 | Zarins et al. |
| 2014/0271717 | A1 | 9/2014 | Goshayeshgar et al. |
| 2014/0303617 | A1 | 10/2014 | Shimada |
| 2014/0336639 | A1 | 11/2014 | Young et al. |
| 2015/0202220 | A1 | 7/2015 | Stein et al. |
| 2015/0265334 | A1 | 9/2015 | Franke et al. |
| 2017/0035496 | A1 | 2/2017 | Nagale et al. |
| 2017/0143409 | A1 | 5/2017 | Taylor et al. |
| 2019/0069949 | A1 | 3/2019 | Vrba et al. |
| 2020/0069366 | A1 | 3/2020 | Clark et al. |
| 2020/0253661 | A1 | 8/2020 | Clark, Jr. et al. |

FOREIGN PATENT DOCUMENTS

| | | |
|---|---|---|
| CN | 104203233 | 12/2014 |
| CN | 105473091 | 4/2016 |
| CN | 112638469 | 4/2021 |
| EP | 3813927 | 6/2024 |
| WO | 2004080384 | 9/2004 |
| WO | 2010057043 | 5/2010 |
| WO | 2013169741 | 11/2013 |
| WO | 2014130031 | 8/2014 |
| WO | 2020047256 | 3/2020 |

OTHER PUBLICATIONS

"Final Office Action," for U.S. Appl. No. 15/357,795 mailed Nov. 30, 2018 (10 pages).
"Final Office Action," for U.S. Appl. No. 15/357,795 mailed Oct. 7, 2019 (14 pages).
"G4 RF Generator," https://www.bostonscientific.com/en-US/products/nerve-radio-frequency-ablation/g4-rf-generator.html available at least as early as Aug. 28, 2018., 4 pages.
"Haylard Coolief Sinergy Cooled Radiofrequency Kit," Instructions for Use, Haylard Sales, LLC, https://www.halyardhealth.com/media/265133/IFU-COOLIEF-SINERGY-Cooled-Radiofrequency-RF-Kit.pdf, Apr. 3, 2015 (84 pages).
"Haylard Health Radiofrequency Pain Management system," https://www.lao.halyardhealth.com/solutions/pain-management/chronic-pain-solutions/radiofrequency-products.aspx, known of at least as early as May 29, 2015., 5 pages.
"International Preliminary Report on Patentability," for PCT Application No. PCT/US2019/048813 mailed Mar. 11, 2021 (9 pages).
"International Search Report and Written Opinion," for PCT Application No. PCT/US2019/048813 mailed Nov. 22, 2019 (14 pages).
"NeuroTherm Simplicity User Manual," Neuro Therm, http://www.cadaverworkshop.info/wp-content/uploads/2012/03/Simplicity-III-Manual.pdf, Mar. 2012 (13 pages).
"Non Final Office Action," for U.S. Appl. No. 15/357,795 mailed Mar. 22, 2019 (11 pages).
"Non-Final Office Action," for U.S. Appl. No. 15/357,795 mailed Sep. 4, 2018 (16 pages).
"Non-Final Office Action," for U.S. Appl. No. 16/553,640 mailed Oct. 17, 2022 (26 pages).
"Non-Final Office Action," for U.S. Appl. No. 16/863,823 mailed May 10, 2022 (21 pages).
"Notice of Allowance," for U.S. Appl. No. 15/357,795 mailed Feb. 5, 2020 (12 pages).
"Notice of Allowance," for U.S. Appl. No. 16/863,823 mailed Aug. 25, 2022 (7 pages).
"NT2000iX Radiofrequency Generator," https://www.neuromodulation.abbott/us/en/hcp/products/radiofrequency-chronic-pain/NT2000iX-radiofrequency-generator.html.html, known of at least as early as May 29, 2015., 3 pages.
"Response to Advisory Action," for U.S. Appl. No. 15/357,795, filed on Feb. 22, 2019 (9 pages).
"Response to Communication Pursuant to Rules 161(1) and 162 EPC," for European Patent Application No. 19769295.7 filed Jul. 23, 2021 (20 pages).
"Response to Final Office Action," for U.S. Appl. No. 15/357,795, filed on Dec. 19, 2018 (9 pages).
"Response to Final Office Action," for U.S. Appl. No. 15/357,795, filed on Jan. 7, 2020 (5 pages).
"Response to Non Final Office Action," for U.S. Appl. No. 15/357,795, filed on Jun. 19, 2019 (9 pages).
"Response to Non Final Office Action," for U.S. Appl. No. 15/357,795, filed on Nov. 6, 2018 (8 pages).
"Response to Non Final Office Action," for U.S. Appl. No. 16/863,823, filed on Jul. 20, 2022 (8 pages).
"Stryker MultiGen 2 Radiofrequency Generator," https://www.stryker.com/us/en/interventional-spine/products/multigen2-rf-generator.html, known of at least as early as May 29, 2015., 2 pages.
"Stryker Venom Cannula and Electrode System," https://www.stryker.com/us/en/interventional-spine/products/venom-cannula-and-electrode-system.html, known of at least as early as May 29, 2015., 2 pages.

(56) References Cited

OTHER PUBLICATIONS

"Stryker Venom Cannula and Electrode System," Stryker Corporation, https://www.stryker.com/us/en/interventional-spine/products/venom-cannula-and-electrode-system.html, 2017 (3 pages).
"The Vessix Renal Denervation System Background Information," Boston Scientific Corporation product factsheet Dec. 12, 2014 (3 pages).
"Vessix Renal Denervation System," Boston Scientific Corporation System Brochure, 2014 (3 pages).
Akassoglou, Katerina, et al."Fibrin Inhibits Peripheral Nerve Remyelination by Regulating Schann Cell Differentiation," Neuron, vol. 33, 861-875, Mar. 14, 2002 (15 pages).
Atwal, Jasvinder K., et al."PriB is a Functional Receptor for Myelin Inhibitors of Axonal Regeneration," Science, vol. 322, Nov. 7, 2008 (5 pages).
Boyd, J.G., et al."A dose-dependent facilitation and inhibition of peripheral nerve regeneration by brain-derived neurotrophic factor," European Journal of Neuroscience, vol. 15, pp. 613-626, 2002 (14 pages).
Christie, Kimberly J., et al."PTEN Inhibition to Facilitate Intrinsic Regenerative Outgrowth of Adult Peripheral Axons," The Journal of Neuroscience, Jul. 7, 2010, 30(27):9306-9315 (10 pages).
Davies, Stephen, et al."Regeneration of Adult Axons in White Matter Tracts of the Central Nervous System," Nature. Dec. 18-25, 1997;390(6661):680-3 (4 pages).
Derry, W. Brent, et al."Substoichiometric Binding of Taxol Suppresses Microtubule Dynamics," Biochemistry, 1995, 34 (7), pp. 2203-2211 (9 pages).
El Bejjani, Rachid, et al."Notch Signaling Inhibits Axon Regeneration," Neuron. Jan. 26, 2012; 73(2):268-278 (20 pages).
Ferrannini, Ele "The Target of Metformin in Type 2 Diabetes," The New England Journal of Medicine 371:16 Oct. 16, 2014 (2 pages).
Fournier, Alyson E., et al."Identification of a receptor mediating Nogo-66 inhibition of axonal regeneration," Nature, vol. 409, Jan. 18, 2001 (6 pages).
Garcia-Perez, Luis-Emilio, et al."Adherence to Therapies in Patients with Type 2 Diabetes," Diabetes Therapy (2013) 4:175-194 (20 pages).
Greene, Lloyd A, et al."Purine Analogs Inhibit Nerve Growth Factor-Promoted Neurite Outgrowth by Sympathetic and Sensory Neurons," J Neurosci. May 1990;10(5):1479-85 (7 pages).
Hanslick, Jennifer, et al."Dimethyl Sulfoxide (DMSO) produces widespread apoptosis in the developing central nervous system," Neurobiology of Disease 34 (2009) 1-10 (10 pages).
Jessen, K.R., et al."The repair Schwann cell and its function in regenerating nerves," J Physiol 594.13(2016) pp. 3521-3531 (11 pages).
Kapural, Leonardo, et al."Radiofrequency Ablation for Chronic Pain Control," Current Pain and Headache Reports 2001, 5:517-525 (9 pages).
Levkovitz, Yechiel, et al."A Dominant Negative Egr Inhibitor Blocks Nerve Growth Factor-Induced Neurite Outgrowth by Suppressing c-Jun Activation: Role of an Egr/c-Jun Complex," The Journal of Neuroscience, May 15, 2002, 22(10):3845-3854 (10 pages).
Maclean, Charles D., et al."Limitations of Diabetes Pharmacotherapy: results from the Vermont Diabetes Information System Study," BMC Family Practice 2006, 7:50 (6 pages).
Park, Kevin Kyungsuk, et al."Promoting Axon Regeneration in the Adult CNS by Modulation of the PTEN/mTOR Pathway," Science. Nov. 7, 2008;322(5903): 963-966 (9 pages).
Pollo, Claudio, et al."Directional Deep Brain Stimulation: an Intraoperative Double-Blind Pilot Study," Brain Jul. 2014; 137(Pt 7):2015-26 (12 pages).
Shen, Yingjie, et al."PTPσ Is a Receptor for Chondroitin Sulfate Proteoglycan, an Inhibitor of Neural Regeneration," Science. Oct. 23, 2009; 326(5952): 592-596 (5 pages).
Smith, Patrice D., et al."SOCS3 deletion promotes optic nerve regeneration in vivo," Neuron. Dec. 10, 2009;64(5): 617-623 (15 pages).
Stichel, Christine C., et al."The CNS Lesion Scar: New Vistas on an Old Regeneration Barrier," Cell Tissue Res. Oct. 1998;294(1):1-9 (9 pages).
Szolcsanyi, Janos, et al."Resiniferatoxin: An Ultrapotent Selective Modulator of Capsaicin-Sensitive Primary Affert Neurons," J Pharmacol Exp Ther. Nov. 1990;255(2):923-8 (6 pages).
Yang, Lynda, et al."Axon Regeneration Inhibitors," Neurol Res. Dec. 2008;30(10):1047-52 (6 pages).
Zhuo, Xiaohui, et al."Lifetim Direct Medical Costs of Treating Type 2 Diabetes and Diabetic Complications," Am. J. Prev. Med. 2013;45(3):253-261 (9 pages).
"Final Office Action," for U.S. Appl. No. 16/553,640 mailed Jan. 10, 2023 (16 pages).
"Response to Non Final Office Action," for U.S. Appl. No. 15/130,031, filed on Jan. 3, 2018 (6 pages).
"Decision of Final Rejection," for Chinese Patent Application No. 201980056878.8 mailed Jul. 5, 2024 (6 pages) with English summary.
"Final Office Action," for U.S. Appl. No. 16/553,640 mailed Jul. 5, 2024 (17 pages).
"Non-Final Office Action," for U.S. Appl. No. 16/553,640 mailed Dec. 21, 2023 (15 pages).
"Office Action," for Chinese Patent Application No. 201980056878.8 mailed Dec. 1, 2023 (11 pages) with English Translation.
"Response to Final Office Action," for U.S. Appl. No. 16/553,640, filed on Apr. 5, 2023 (11 pages).
"Response to Non Final Office Action," for U.S. Appl. No. 16/553,640, filed on Mar. 20, 2024 (9 pages).
"Second Office Action," for Chinese Patent Application No. 201980056878.8 mailed May 8, 2024 (5 pages) with English summary.

\* cited by examiner

DEVICES AND METHODS FOR ENHANCED DENERVATION PROCEDURES

PRIORITY

This application is a continuation of U.S. patent application Ser. No. 16/863,823, filed Apr. 30, 2020, a divisional of U.S. patent application Ser. No. 15/357,795, filed Nov. 21, 2016, which claims the benefit of priority under 35 U.S.C. § 119 to U.S. Provisional Application Ser. No. 62/258,986, filed Nov. 23, 2015, which is incorporated by reference in its entirety and for all purposes.

FIELD

The present disclosure relates to methods, devices, kits and systems for enhancing the efficacy and longevity of denervation procedures.

BACKGROUND

Existing technology used for denervation for chronic pain primarily includes radiofrequency ablation (RFA), which is commonly performed in a monopolar configuration where current is passed between a probe and a ground pad. Unfortunately, nerve fibers regenerate over time, leading to the need for repeated denervation procedures for the management of pain.

The present disclosure pertains to devices and methods for use in inhibiting nerve regeneration after the performance of denervation procedures, including RFA denervation procedures, among others, for the treatment of pain, as well as numerous other therapies as detailed below.

SUMMARY

In some aspects of the present disclosure, a method of treatment is provided, which comprises (a) conducting a denervation procedure at a target site in a subject, (b) introducing at least one agent that inhibits or prevents nerve regeneration to the target site and (c) optionally introducing an anesthetic agent to the target site.

In some aspects of the present disclosure, a system is provided, which comprises (a) means for conducting a denervation procedure at a target site in a subject and (b) means for introducing at least one agent that inhibits or prevents nerve regeneration to the target site and (c) optional means for introducing one or more anesthetic agents to the target site In some embodiments, which may be used in conjunction with any of the preceding aspects, the denervation procedure may be a radiofrequency ablation (RFA) procedure.

In some embodiments, which may be used in conjunction with any of the above aspects and embodiments, the at least one agent that inhibits or prevents nerve regeneration may be a chemical agent. In some instances, the chemical agent may be introduced to the target site as an injectable composition, which may be, for example, in the form of a solution, a gel or a dispersion of particles, among other possible forms. Alternatively or in addition, the chemical agent may be introduced to the target site as an encapsulated solid, liquid, gel or dispersion. Alternatively or in addition, the chemical agent may be introduced to the target site by filling a reservoir by injection in vivo, in which case the reservoir may optionally comprise one or more surface electrodes. Alternatively or in addition, a device that contains the chemical agent may be clamped around a severed nerve and wherein the device exposes the severed nerve to the chemical agent.

In some embodiments, which may be used in conjunction with any of the above aspects and embodiments, a solid material may be provided at the target site. In some instances, the solid material may comprise an imaging agent. Alternatively or in addition, the solid material may comprise a chemical agent that inhibits or prevents nerve regeneration.

In some embodiments, which may be used in conjunction with any of the above aspects and embodiments, a solid material may be formed at the target site.

In some embodiments, which may be used in conjunction with any of the above aspects and embodiments, a solid material may be introduced to the target site. For example, the solid material may be a detachable material that may be positioned at a distal end of a medical device, which may be, for instance, an ablation device, among other possibilities.

In some embodiments, which may be used in conjunction with any of the above aspects and embodiments, a solid material may be introduced to the target site in the form of a detachable sheath. In some instances, the medical device may comprise an ablation electrode and the detachable sheath may be disposed over the ablation electrode. Alternatively or in addition, the medical device may comprise a lumen through which a vacuum source applied to the detachable sheath. Alternatively or in addition, the detachable sheath may comprise an agent or device that causes an ablated nerve to grow into the sheath.

In some aspects, the present disclosure provides a radiofrequency ablation device that comprises (a) a needle electrode configured to perform a radiofrequency ablation procedure and (b) a detachable sheath disposed over the needle electrode.

In some embodiments, the sheath of the radiofrequency ablation device may be crumpled when detached from the needle electrode.

In some embodiments, which may be used in conjunction with any of the above aspects and embodiments, the sheath may comprise one or more chemical agents. The one or more chemical agents may be, for example, released from the sheath after detachment of the sheath within a subject. The one or more chemical agents may comprise, for example, an agent that inhibits or prevents nerve regeneration, an anesthetic agent, or a combination of both.

In some aspects, the present disclosure provides a device that may be configured to clamp around and sever a nerve fiber and release a chemical agent that inhibits or prevents nerve regeneration in the presence of the severed nerve fiber. The device may comprise, for, example, one or more blades configured to sever the nerve fiber.

In some aspects, the present disclosure provides a kit that comprises (a) an implantable reservoir and (b) a catheter, wherein the implantable reservoir is configured to inhibit or prevent nerve regeneration at a target site in a patient.

In some embodiments, which may be used in conjunction with any of the preceding aspects, the catheter may be configured to deliver radiofrequency ablation energy to the target site. In certain of these embodiments, the implantable reservoir may comprise electrodes and the catheter may be configured to deliver the radiofrequency ablation energy to the electrodes.

In some embodiments, which may be used in conjunction with any of the above aspects and embodiments, the reservoir may be configured to release at least one agent that inhibits or prevents nerve regeneration at the target site. The at least one agent that inhibits or prevents nerve regeneration may be introduced, for example, in the form of a solution, a gel, a dispersion, or a solid material, among others.

In certain embodiments, which may be used in conjunction with any of the above aspects and embodiments, the implantable reservoir may comprise a lumen that is configured to receive the at least one agent that inhibits or prevents nerve regeneration, and the catheter may be configured to introduce the at least one agent that inhibits or prevents nerve regeneration into the lumen at the target site. The implantable reservoir may be an inflatable implantable reservoir in certain instances.

In certain embodiments, which may be used in conjunction with any of the above aspects and embodiments, the catheter may comprises a needle electrode configured to perform a radiofrequency ablation procedure, and the implantable reservoir may comprise a detachable sheath that is disposed over the needle electrode. The detachable sheath may, for example, become crumpled when detached from the needle electrode. The detachable sheath may, for example, release a chemical agent that inhibits or prevents nerve regeneration after detachment of the sheath within a subject. The detachable sheath may, for example, comprise an agent that causes an ablated nerve to grow into the sheath. The catheter may, in certain cases, comprise a lumen through which a vacuum source is applied to the detachable sheath.

In certain embodiments, which may be used in conjunction with any of the above aspects and embodiments, the implantable reservoir may comprise a device that is configured to clamp around and sever a nerve fiber and release at least one agent that inhibits or prevents nerve regeneration in the presence of the severed nerve fiber. In certain cases, the device may comprise one or more blades configured to sever the nerve fiber.

In certain embodiments, which may be used in conjunction with any of the above aspects and embodiments, the kit may be configured to introduce an anesthetic agent to the target site.

Other aspects and embodiments, as well as various advantages of the present disclosure will become immediately apparent to those of ordinary skill in the art upon review of the detailed description and claims to follow

DETAILED DESCRIPTION

Figure 1A:
FIGS. 1A-1D are schematic side views illustrating a denervation procedure in accordance with an embodiment of the present disclosure.

The devices and methods of the present disclosure are useful in a variety of denervation treatments, including denervation therapy at an anatomical location for targeted relief of chronic pain (e.g. facet joint, sacroiliac joint, knee, foot, and hip), as well as clinical denervation procedures for the treatment of hypertension, including pulmonary arterial hypertension, asthma, chronic obstructive pulmonary disease (COPD), diabetes, metabolic syndrome, heart failure, arrhythmias, chronic kidney disease, obstructive sleep apnea and overactive bladder, among others, and may be used in conjunction with various denervation techniques, including denervation based on radiofrequency energy (including conventional monopolar RF, bipolar RF, multipolar RF), laser energy, ultrasound (e.g., high intensity focused ultrasound) and microwave energy sources, cryogenic denervation procedures, and chemical denervation procedures, among others.

Thus, while the devices and methods of the present disclosure are typically described herein in the context of RF ablation procedures, in many cases, they are applicable to other ablation procedures as well.

In various embodiments, the present disclosure is directed to devices and methods for inhibiting nerve regeneration following a denervation procedure, which utilize chemical agents that inhibit or prevent nerve regrowth (also referred to as "agents that inhibit or prevent nerve regeneration" or simply "anti-regeneration agents"). These agents include inorganic and organic chemical agents, including small molecule organic chemical agents, biochemical agents, which may be derived from the patient and/or from an external source such as an animal source and/or a synthetic biochemical source, and cell-based therapies.

Some specific examples of anti-regeneration agents that may be used in conjunction with the present disclosure include the following, among others: (a) capsaicin, resiniferatoxin and other capsaicinoids (see, e.g., J. Szolcsanyi et al., "Resiniferatoxin: an ultrapotent selective modulator of capsaicin-sensitive primary afferent neurons", *JPharmaco/Exp Ther.* 1990 November; 255(2):923-8); (b) taxols including paclitaxel and docetaxel (i.e., at concentrations are sufficiently elevated to slow or cease nerve regeneration, as lower concentrations of paclitaxel may facilitate nerve regeneration; see, e.g., W. B. Derry, et al., "Substoichiometric binding of taxol suppresses microtubule dynamics," *Biochemistry* 1995 Feb. 21; 34(7):2203-11), botox, purine analogs (see, e.g., LA Greene et al., "Purine analogs inhibit nerve growth factor-promoted neurite outgrowth by sympathetic and sensory neurons," *The Journal of Neuroscience,* 1 May 1990, 10(5): 1479-1485); (c) organic solvents (e.g., acetone, aniline, cyclohexane, ethylene glycol, ethanol, etc.); (d) vinca alkaloids including vincristine, vindesine and vinorelbine, and other anti-microtubule agents such as nocodazole and colchicine; (e) platinum-based antineoplastic drugs (platins) such as cisplatin, carboplatin, oxaliplatin, satraplatin, picoplatin, nedaplatin and triplatin; (f) $ZnSO_4$ (i.e., neurodegenerative factor); (g) latarcins (short linear antimicrobial and cytolytic peptides, which may be derived from the venom of the spider *Lachesana tarabaevi*); (h) chondroitin sulfate proteoglycans (CSPGs) such as aggrecan (CSPG1), versican (CSPG2), neurocan (CSPG3), melanoma-associated chondroitin sulfate proteoglycan or NG2 (CSPG4), CSPG5, SMC3 (CSPG6), brevican (CSPG7), CD44 (CSPG8) and phosphacan (see, e.g., Shen Y et al. "PTPsigma is a receptor for chondroitin sulfate proteoglycan, an inhibitor of neural regeneration", *Science,* 2009 Oct. 23; 326(5952):592-6); (i) myelin-associated glycoprotein (MAG); (j) oligodendrocytes; (k) oligodendrocyte-myelin glycoprotein; and (l) Reticulon-4, also known as Neurite outgrowth inhibitor or Nogo, which is a protein that in humans is encoded by the RTN4 gene (see, e.g., Lynda J.-S. Yang et al., "Axon regeneration inhibitors, *Neurological Research*, 1 Dec. 2008, Volume 30, Issue 10, pp. 1047-1052).

Further examples of anti-regeneration agents suitable for use in the present disclosure include agents that induce the formation of a glial scar which has been shown to inhibit nerve regeneration after spinal cord injury, which may be selected from the following, among others: (a) laminin, fibronectin, tenascin C, and proteoglycans, which have been shown in inhibit axon regeneration (see, e.g., Stephen J. A. Davies et al., "Regeneration of adult axons in white matter tracts of the central nervous system," *Nature* 390, 680-683 (18 Dec. 1997); (b) reactive astrocyte cells, which are the main cellular component of the glial scar, which form dense web of plasma membrane extensions and which modify extracellular matrix by secreting many molecules including laminin, fibronectin, tenascin C, and proteoglycans; (c) molecular mediators known to induce glial scar formation including transforming growth factor β (TGF β) such as TGFβ-1 and TGFβ-2, interleukins, cytokines such as interferon-γ (IFNγ), fibroblast growth factor 2 (FGF2), and ciliary neurotrophic factor; (d) glycoproteins and proteoglycans that promote basal membrane growth (see, e.g., CC Stichel et al., "The CNS lesion scar: new vistas on an old regeneration barrier", *Cell Tissue Res*. (October 1998) 294 (1): 1-9); and (e) substances that deactivate Schwann cells.

Still other examples of anti-regeneration agents for use in the present disclosure include Semaphorin-3A protein (SEMA3A) (which may be used to induce the collapse and paralysis of neuronal growth cones), calcium (which may lead to turning of nerve growth cones induced by localized increases in intracellular calcium ions), methylene blue, and radioactive particles.

As noted above, in certain cases, anti-regeneration agents may be obtained from the subject being treated. For example, a needle may be used for suctioning, cutting and aspirating nerve fibers. The aspirate may then be processed to extract and concentrate anti-regeneration factors present such as Nogo, chondroitin sulfate proteoglycans and other glycoproteins (e.g., in the form of a liquid extract, sheet, fiber, powder, etc.), which may be injected to the site of ablation post-processing, for example, via member left in place at the target site (e.g., a hollow needle used for RFA, through which the anti-regeneration factors may be introduced, as discussed below).

Additionally, certain aspects of the invention will relieve the patient of pain in the short-term post-procedure timeframe where increased pain over baseline may be experienced due to local tissue reaction to the ablation procedure. Examples of suitable anesthetic agents for this purpose include, for instance, bupivicaine, ropivicane, lidocaine, or the like, which can be released to provide short-term local pain relief post-procedure around the treatment region.

The anesthetic agent may be released over a timeframe of 14 days or less, preferably 7 days or less. The anti-regeneration agent may be released over an appropriate timeframe, or at specific intervals in time, for the particular agent to effectively block nerve regeneration from occurring.

In various aspects, the devices and methods of the present disclosure may achieve a longer-lasting denervation effect (i.e., significantly longer than the current ~9 months achieved with RFA) than that observed in the absence of such devices and methods.

Figure 1B:
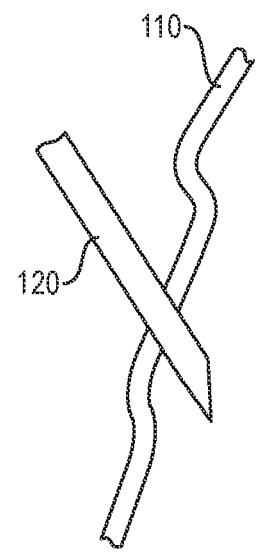
Figure 1C:
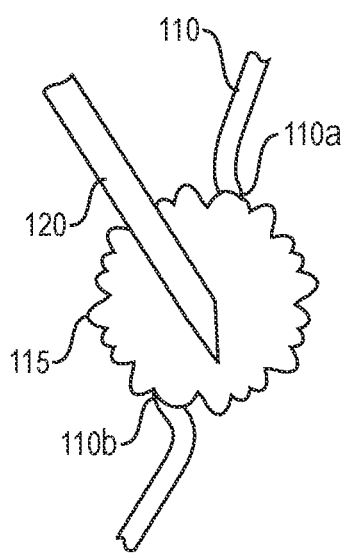

Turning now to the figures, in one embodiment, a nerve fiber 110 as shown in FIG. 1A is accessed by an energy-emitting probe, for example, an RF ablation electrode 120 in the form of a needle as shown in FIG. 1B. Upon application of energy to the electrode 120 a region of ablated tissue 115, including ablated nerve fiber, may be formed as shown in FIG. 1C. Without further steps, nerve fiber will typically regenerate between axon ends 110*a*, 110*b* over a period of time, typically around 6 to 18 months.

In accordance with the present disclosure, however, at least one anti-regeneration agent may be introduced at the site at the time of treatment (e.g., before, during and/or after ablation), thereby delaying or eliminating the need for a subsequent ablation treatment for the patient. In certain instances, an anesthetic agent may also be introduced to the treatment site to address any short term pain associated with the procedure.

Figure 1D:
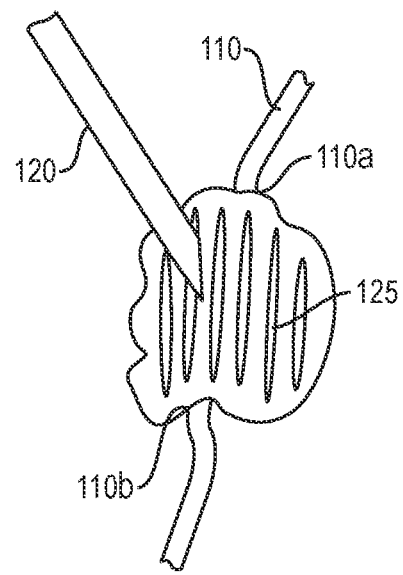

In the particular embodiment shown, the electrode 120 employed in the RFA procedure is provided with an internal lumen (not shown) through which an injectable composition containing one or more anti-regeneration agents 125 (also referred to herein as an "anti-regeneration composition") can be delivered to the ablation site as shown in FIG. 1D. This is particularly desirable in that the ablation electrode 120 is already positioned at the precise site of nerve destruction, and thus the site where inhibition or prevention of nerve regeneration is desired.

Figure 2:
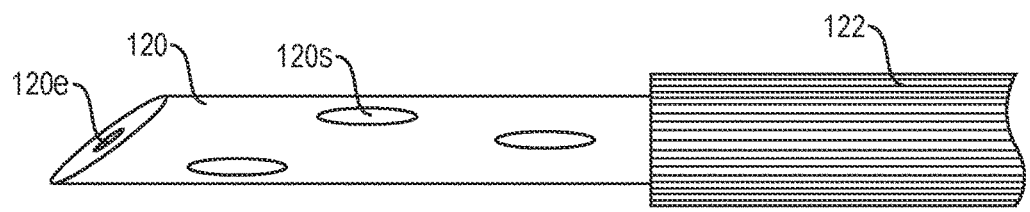
FIG. 2 is a schematic side view of an ablation device, in accordance with an embodiment of the present disclosure.

In certain embodiments, the needle electrode(s) employed may be, for instance, small diameter (e.g., 16 gauge or smaller) and may include one or more lumens through which the anti-regeneration composition may be injected. The anti-regeneration composition may be injected, for example, from at least one needle electrode 120 that contains an end opening or one or more side openings or, as illustrated in FIG. 2, both an end opening 120*e* and one or more side openings 120*s*. The needle electrode 120 may also contain an insulting sheath 122 to prevent ablation in regions other than at or near the electrode tip, as is known in the art. In some embodiments, coolant may be introduced through the electrode (i.e., in an open-irrigated RFA procedure) in order to maintain lower tissue temperatures near the probe tip and allow larger lesion sizes to be achieved. Anti-regeneration agent may be introduced with the coolant or as a separate injectable anti-regeneration composition. The holes may be round, oval, triangular, square, or essentially any other regular or irregular shape. Typical hole dimensions may range, for example, from 0.002" (0.05 mm) to 0.020" (0.5 mm) in width, among other possible values. In certain embodiments, the holes may be preferentially located radially around the needle to allow directionality in the introduction of injectable media.

Examples of injectable anti-regeneration compositions include solutions that contain one or more anti-regeneration agents, including higher viscosity solutions and gels (ranging, for example, up to 100,000 cp or more, with the preferred value depending upon needle size, among other variables). Other examples of injectable anti-regeneration compositions include fluids that contain particles of the anti-regeneration agent, including higher viscosity particle dispersions and gels. The particles in the particle-containing fluids may be in the form of, for example, (a) solid particles of anti-regeneration agent, (b) solid particles comprising anti-regeneration agent dissolved or dispersed in a solid matrix material, (c) encapsulated solid particles of anti-regeneration agent, (d) encapsulated particles comprising anti-regeneration agent dissolved or dispersed in a solid matrix material, and (e) encapsulated solutions, dispersions or gels comprising anti-regeneration agent. Mechanisms for release of anti-regeneration agent from such particles include bioerosion (e.g., due to particle dissolution, biodegradation, etc.), diffusion, or a combination of bioerosion and diffusion. In certain embodiments, the encapsulation material may comprise an anesthetic for shorter term pain relief.

Examples of matrix materials and encapsulation materials include various synthetic biostable or biodegradable polymers, various naturally occurring polymers, as well as various biologics.

Examples of synthetic biostable polymers may be selected from the following: (a) polyolefin homopolymers and copolymers, including homopolymers and copolymers of C2-C8 alkenes, for example, polyethylene and polypropylene among others, (b) fluoropolymers, including homopolymers and copolymers of C2-C8 alkenes in which one or more hydrogen atoms are substituted with fluorine, for example, polytetrafluoroethylene (PTFE), polyvinylidene fluoride (PVDF), poly(vinylidene fluoride-co-hexafluoropropene) (PVDF-HFP) among others, (c) polyamides such as nylons, among others, (d) polyesters, including, for example, polyethylene terephthalate, among others, (e) styrenic copolymers such as isobutylene-styrene copolymers, including block copolymers comprising one or more polystyrene blocks and one or more polyisobutylene blocks, for instance, poly(styrene-b-isobutylene-b-styrene) (SIBS), among others, (e) polyurethanes such as polyisobutylene based polyurethanes (PIB-PU), among others, (f) as well as various other non-absorbable polymers such as siloxanes or silicones.

Examples of synthetic biodegradable polymers may be selected, for example, from polyesters and polyanhydrides, among others. Specific biodegradable polymers may be selected from suitable members of the following, among others: (a) polyester homopolymers and copolymers (including polyesters and poly[ester-amides]), such as polyglycolide, polylactide (PLA), including poly-L-lactide, poly-D-lactide, and poly-D,L-lactide, poly(lactide-co-glycolide) (PLG), including poly(L-lactide-co-glycolide), poly(D-lactide-co-glycolide) and poly(D,L-lactide-co-glycolide), poly(beta-hydroxybutyrate), poly-D-gluconate, poly-L-gluconate, poly-D,L-gluconate, poly(epsilon-caprolactone), poly(delta-valerolactone), poly(p-dioxanone), poly(trimethylene carbonate), poly(lactide-co-delta-valerolactone), poly(lactide-co-epsilon-caprolactone), poly(lactide-co-beta-malic acid), poly(lactide-co-trimethylene carbonate), poly(glycolide-co-trimethylene carbonate), poly(beta-hydroxybutyrate-co-beta-hydroxyvalerate), poly[1,3-bis(p-carboxyphenoxy)propane-co-sebacic acid], poly(sebacic acid-co-fumaric acid), and poly(ortho esters) such as those synthesized by copolymerization of various diketene acetals and diols, among others; and (b) polyanhydride homopolymers and copolymers such as poly(adipic anhydride), poly(suberic anhydride), poly(sebacic anhydride), poly(dodecanedioic anhydride), poly(maleic anhydride), poly[1,3-bis(p-carboxyphenoxy)methane anhydride], and poly[alpha,omega-bis(p-carboxyphenoxy)alkane anhydrides] such as poly[1,3-bis(p-carboxyphenoxy)propane anhydride] and poly[1,3-bis(p-carboxyphenoxy)hexane anhydride], among others.

Where copolymers are employed, copolymers with a variety of monomer ratios may be available. For example, where PLG is used, a variety of lactide:glycolide molar ratios will find use herein, and the ratio is largely a matter of choice, depending in part on the rate of degradation desired. For example, a 50:50 PLG polymer, containing 50% D,L-lactide and 50% glycolide, will provide a faster resorbing copolymer, while 75:25 PLG degrades more slowly, and 85:15 and 90:10, even more slowly, due to the increased lactide component. Degradation rate can also be controlled by such factors as polymer molecular weight and polymer crystallinity.

Examples of naturally occurring polymers include biostable and biodegradable polymers such as cellulose, biocellulose, and alginates (non-crosslinked and ionically crosslinked).

As defined herein, a "biologic material" is a material that comprises one or more extracellular matrix components. Biologic materials for use herein include crosslinked and non-crosslinked allograft (e.g., human cadaveric) materials, as well as crosslinked and non-crosslinked heterograft (e.g., bovine, porcine, equine, etc.) materials. Specific examples of non-crosslinked biologic materials include mammalian non-crosslinked biologic matrix materials, such as human dermis, human fascia lata, fetal bovine dermis and porcine small intestinal submucosa. Specific examples of crosslinked biologic materials include mammalian crosslinked biologic materials such as crosslinked porcine dermis, crosslinked porcine small intestinal submucosa, crosslinked bovine pericardium, and crosslinked horse pericardium. Such materials are typically acellular. Moreover, they are typically predominantly collagen. Such biologic materials may be, for example, processed into an injectable gelatinous material useful as a carrier for anti-regeneration agents. For example, small flat particles of such biologic materials may be provided in conjunction with a suitable injection formulation. Upon injection, such particles may form a physical barrier to nerve growth, without imposing an insurmountable barrier for agent release. In such embodiments, particle size may be varied to change diffusion rates.

Examples of injectable anti-regeneration compositions for use herein include compositions that solidify in the body. For example, a hydrogel precursor material that contains one or more anti-regeneration agents, for example, in dissolved or particle form, may be injected into the patient. In some embodiments, a crosslinkable fluid formulation that contains one or more anti-regeneration agents, for example, in dissolved or particle form, may be employed as an injectable anti-regeneration composition that solidifies in the body. The crosslinks that may be formed include covalent crosslinks hydrogen bonding crosslinks and physical crosslinks or entanglements. Crosslinking may be promoted by residual heat after ablation, high ion concentrations (e.g., from a saline cooling agent, where employed), additional low-level applied RF energy and pH changes, among other mechanisms. In some embodiments, a solution containing one or more organic solvents, one or more dissolved polymers, and one or more anti-regeneration agents, for example, in dissolved or particle form, may be employed as an injectable anti-regeneration composition that solidifies in the body. In these embodiments, the dissolved polymer may precipitate as the organic solvent(s) are absorbed by the body of the subject. Chemically sensitive (unstable) anti-regeneration agents may be encapsulated by biostable or biodegradable polymers to protect them from solvents and chemical degradation from crosslinking reactions. In this manner the purity and chemical structure of anti-regeneration agent would be maintained.

It should be noted that where a solid or solidifiable composition is introduced into a subject, the composition may provide a mechanical barrier to nerve regeneration alternatively or in addition to releasing an anti-regeneration agent, for example, by diffusion through porous materials and solid materials (e.g., where the anti-regeneration agent is a small molecule agent), among other mechanisms.

In various aspects of the present disclosure, ablation devices are provided that have one or more components detachably connected to the distal region of the device, which act to inhibit or prevent nerve regeneration upon being deposited in the body. Such devices may also contain a reservoir having the capacity to store and disperse anti-regeneration agents.

Figure 3A:
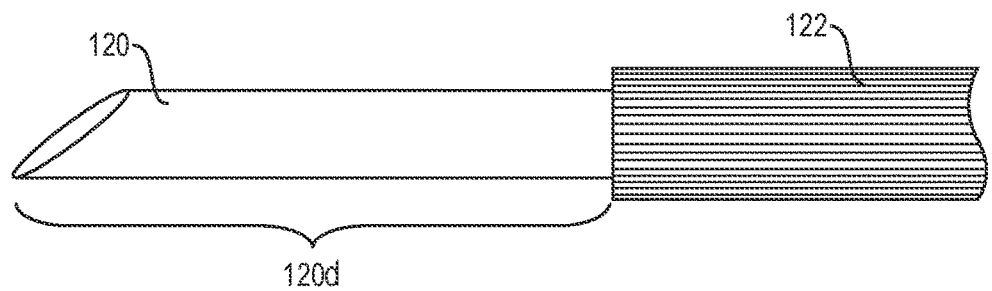
FIG. 3A is a schematic side view of an ablation device, in accordance with an embodiment of the present disclosure.
Figure 3B:
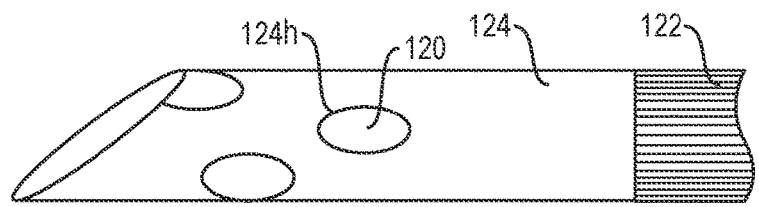
FIGS. 3B-3D are schematic side views of detachable sheaths, in accordance with three embodiments of the present disclosure.

In some embodiments, for example, an ablation electrode may be provided with a detachable anti-regeneration-agent-releasing sheath that can be delivered to the ablation site for this purpose. As a specific example, a treatment device comprising a needle electrode 120 and insulting sheath 122 like that shown in FIG. 3A may be provided with an a leave-behind sheath 124 that covers the exposed distal end 120d of the needle electrode as shown in FIG. 3B. In the embodiment shown, the sheath 124 is provided with discrete holes 124h that allow or enhance the passage of current between the underlying needle electrode 120 and the surrounding environment. Although the leave-behind sheath 124 shown has discrete holes 124h, in other embodiments, the leave-behind sheath 124 may be of a micro-porous structure with hundreds, thousands, millions, or even more small pores through which current may pass.

In addition, the needle electrode 120 may include one or more lumens through which an additional anti-regeneration-agent-containing composition or an anesthetic-agent-containing composition may be injected (see, e.g., FIG. 2). Alternatively or in addition, saline or other fluid may be injected through the one or more lumens, which may wet the leave-behind sheath to enhance energy transfer and/or to cool the tip (in an open-irrigated manner).

In embodiments where a leave-behind sheath is provided, the anti-regeneration agent may be provided in a layer that is disposed over an underlying sheath material. For example, the layer may be a layer of anti-regeneration agent per se, or the layer may be in the form of a matrix material within which the anti-regeneration agent is dissolved or within which particles of the anti-regeneration agent are dispersed. If desired, an overlying layer may be provided in certain instances which acts to slow release of the anti-regeneration agent and/or which may comprise an anesthetic agent for shorter term pain relief.

Alternatively or in addition, an anti-regeneration agent may be provided within the sheath-forming material. For example, the sheath-forming material may act as a matrix material within which the anti-regeneration agent is dissolved or within which particles of the anti-regeneration agent are dispersed. If desired, an overlying layer may be provided in certain instances which acts to slow release of the anti-regeneration agent and/or which comprises an anesthetic agent for shorter term pain relief.

Examples of matrix materials and materials for overlying layers include various synthetic biostable or biodegradable polymers, various naturally occurring polymers, as well as various biologics, such as those set for above. As with the particulate forms described above, mechanisms for release of anti-regeneration agent include bioerosion (e.g., due to particle dissolution, biodegradation, etc.), diffusion, or a combination of bioerosion and diffusion.

Figure 3C:
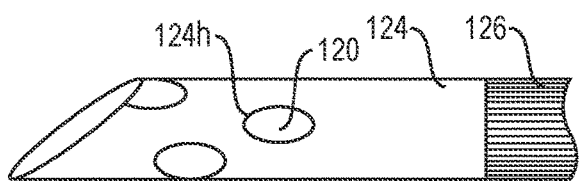

After treatment with the needle electrode 120 has been completed, the needle electrode 120 is removed and the sheath 124 is left behind for long-term delivery of anti-regeneration agent and, optionally, short term delivery of anesthetic agent. In some embodiments, the leave-behind sheath 124 may be detachably secured over the needle electrode 120 such that the sheath 124 slips off of the needle electrode 120 when it is retracted from the treatment site. In other embodiments, the insulting sheath 122 may be configured such that it can be advanced relative to the needle electrode 120, such that the leave-behind sheath 124 is pushed from the distal tip of the needle electrode 120. In still other embodiments, the position of the needle electrode 120 and insulating sheath 122 may remain fixed, and a separate sheath 126 (see, e.g., FIG. 3C) may be advanced over the insulating sheath 122 and engage the leave-behind sheath 124, thereby pushing the leave-behind sheath 124 from the distal tip of the needle electrode 120.

Figure 3D:
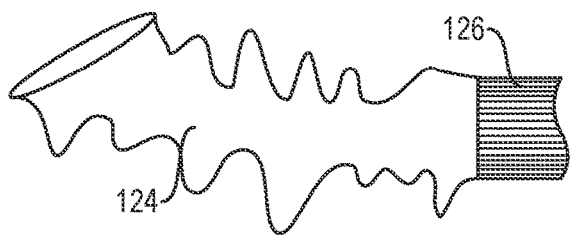

In certain embodiments, the leave-behind sheath 124 may crumple when pushed from the distal tip of the needle electrode 120 as shown in FIG. 3D. In other embodiments, the sheath 124 may substantially retain its shape when pushed from the distal tip of the needle electrode 120, thereby maintaining its inner lumen to serve additional functions such as those described below.

One specific example of the steps that may be employed in the use of a leave-behind sheath follows: (a) insert device to target location, (b) confirm placement via an appropriate method (e.g. fluoroscopic, ultrasound, stimulation, etc.), (c) deliver therapeutic energy (e.g. radiofrequency energy), (d) push the insulative sheath while pulling the conductive element associated with the electrode, causing the leave-behind sheath to be pushed beyond the distal tip of the needle electrode, (e) if necessary, twist the insulative sheath gently to finish detachment from the leave-behind sheath, and (f) remove insulative sheath and conductive element.

In certain embodiments, the leave-behind sheath may be provided with a lumen that can be attached to a vacuum source for suction, allowing a nerve ending to be drawn into the sheath subsequent to ablation, thereby preventing the nerve ending from rejoining with another.

In certain embodiments, an electromagnetic source, a chemical attractant such as an agent that provides an electrochemical "pulse," and/or another agent that attracts generation of previously ablated nerve may be associated with the leave-behind sheath (e.g., placed within the leave-behind sheath lumen), causing the nerve to grow into the sheath lumen and terminate, thus preventing the axon ends from re-attaching/growing back together. For example, one or more chemicals, such as those naturally present in the body that contribute to nerve regeneration, may be disposed inside the conduit to attract the nerve and cause the nerve to grow into the conduit. As another example, electromagnetic pulses, at specific frequencies and burst patterns, may be generated to attract nerve ends into the conduit. In some instances, the specific frequencies and burst patterns employed may be based on the particular nerve being targeted, as each peripheral nerve may have different intrinsic action potential firing rates. Electromagnetic pulses may be applied, for example, via a conventional or miniature implantable pulse generator (IPG) associated with the conduit and/or via inductive coupling to provide energy via an external signal generator. The frequency of pulses and/or bursts of pulses may range, for example, between 1 and 100 Hertz, among other values. Electromagnetic sources may further include light sources, for example, LED light sources, among others, which may be placed inside the conduit to attract the nerve ending to regenerate into the conduit. In some cases, the conduit may have only one entrance. In some cases, the conduit may contain one or more anti-regeneration agents such as those described above, to prevent the nerve from growing further.

Alternatively, the nerve may be captured within a lumen of a sheath (e.g., by suction), where it may be, for example, treated with a suitable energy source or sink (e.g., RF energy, laser, ultrasound, cryogenic treatment, etc.), mechanically cut, or chemically ablated (e.g., using ethanol or another chemical agent). Subsequently, the ends may optionally be capped, for example, by injecting a crosslinkable polymer formulation into the sheath. After treatment, the sheath may be left behind, for example, using one of the approaches described above.

In other aspects of the present disclosure, anti-regeneration agent may be released at a site of ablation by filling a reservoir by injection in vivo and subsequently allowing the anti-regeneration agent to be released from the reservoir.

Figure 4:
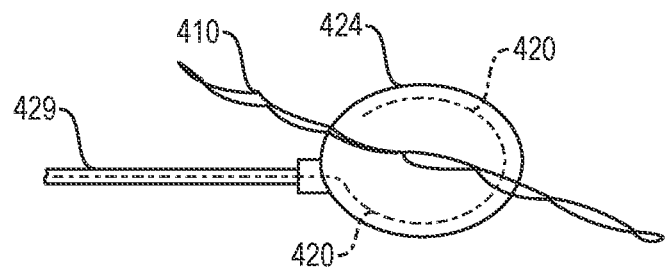
FIG. 4 is a schematic side view illustrating an ablation device being used in conjunction with an ablation procedure, in accordance with an embodiment of the present disclosure.

For example, and with reference to FIG. 4, a deflated and detachable balloon reservoir 424 may be inserted into a site adjacent a nerve 410 to be treated (for example, using a suitable imaging modality such as x-ray or ultrasound imaging, among other possibilities). The balloon reservoir 424 is connected to a catheter 429 that can be removed at the end of the procedure. The reservoir 424 may be inflated through a lumen of the catheter 429, which inflation can cause a mechanical compression effect on the nerve 410. The inflation medium may be, for example, saline, or may contain one or more anti-regeneration agents such as those described elsewhere herein (e.g., myelin associated glycoprotein (MAG), oligodendrocyte-myelin glycoprotein (OMpg), chondroitin sulfate proteoglycans, etc.), allowing the reservoir to be filled with anti-regeneration agent. The reservoir may be provided, for example, with a one-way valve to prevent escape of the inflation fluid along the route by which it is introduced. The one or more anti-nerve regeneration substances are subsequently slowly released from the reservoir 424 for example, by diffusion through the reservoir wall or by seeping out of pores that are formed in the reservoir wall, among other possible mechanisms.

The reservoir may also be provided with electrodes 420 for RF ablation. For instance, RF ablation may be conducted at the time of inflation by supplying energy to the electrodes 420 via a catheter 429 in the form of a hollow conductor (which may be provided with an insulative coating as described above). In certain embodiments, the electrodes 420 may be energized wirelessly, circumventing the need for a conductor-containing catheter 429.

In certain embodiments, a catheter 429 may be inserted at a later date for re-inflation of the reservoir 424 and/or to conduct additional ablation procedures. The reservoir 424 may further be provided with a suitable marking structure (e.g., a structure visible under ultrasound, fluoroscopy, etc.) to locate the reservoir 424 for future insertions, ablations and inflations. In certain embodiments, the reservoir 424 may be removed by deflating the reservoir 424 after a predetermined period of time.

Figure 5:
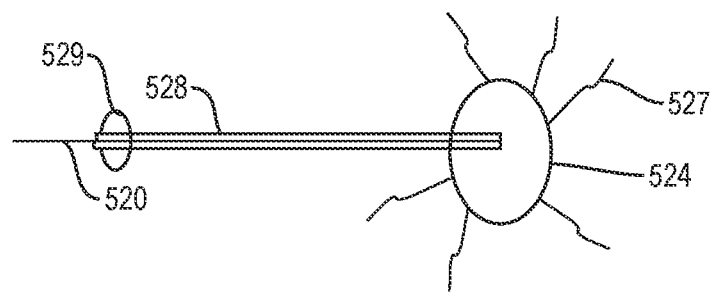
FIG. 5 is a schematic side view of an ablation device, in accordance with an embodiment of the present disclosure.

In a related embodiment, and with reference to FIG. 5, an electrode (e.g., a hollow needle-shaped electrode structure 520) may be introduced into a treatment site, while inserted into a tubular shaft 528 associated with a balloon-like structure 524, at which point an ablation procedure is performed using the electrode structure 520. Subsequently, the balloon may be inflated with a suitable inflation fluid, for example, saline or a fluid containing one or more anti-regeneration agents as described above. The balloon 524 may be further provided with barbs 527 to secure the balloon 524 to surrounding tissue. Where formed of a conductive material and in electrical communication with an inserted conductor, the barbs 527 may also function as electrodes for RF ablation. After inflation, electrode structure 520 may be removed, leaving the balloon 524 and shaft 528 in the patient. The shaft 528 may further be provided with a magnetic ring 529 or other suitable marking structure (e.g., a structure visible under ultrasound, fluoroscopy, etc.) to locate the structure for future insertions, ablations and inflations. In certain embodiments, the balloon 524 and tubular shaft 528 may be left behind just under the skin surface.

Figure 6:
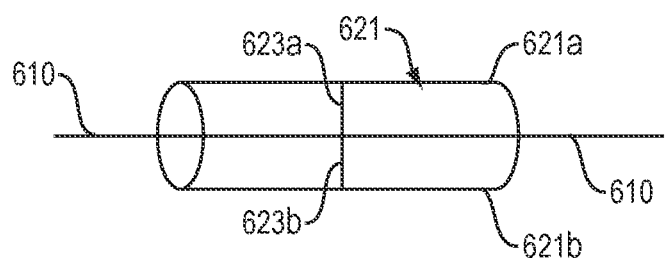
FIG. 6 is a schematic side view illustrating an ablation device being used in conjunction with an ablation procedure, in accordance with an embodiment of the present disclosure.

In other aspects of the present disclosure, a device may be provided which is clamped around a nerve fiber, severing the nerve fiber, and which may also create an anti-regeneration-agent-containing environment around the severed nerve ends. For example, referring now to FIG. 6, a device 621 is shown, which includes two hinged semi-cylindrical pieces 621a, 621b, which have been closed around a nerve fiber 610. The device further includes at least one cutting member, specifically, blades 623a, 623b that meet and sever the nerve fiber 610, when the semi-cylindrical pieces 621a, 621b are snapped shut around the nerve fiber. The cutting member may then act as a barrier to nerve regeneration. Alternatively, or in addition, the device 621 may further be provided with at least one anti-regeneration agent. For example, the semi-cylindrical pieces 621a, 621b may contain and elute an anti-regeneration agent, or an anti-regeneration-agent-containing composition, for instance, in the form of an anti-regeneration-agent-containing liquid, gel or solid, may be included in the interior of the device.

As previously suggested, an additional potential feature of any solid material described herein that is implanted in the patient (e.g., compositions that solidify in the body, leave-behind sheath, inflatable reservoir, cutting device) may be provided with a suitable imaging contrast agent that serves as a "marker" for subsequent procedures should they be needed. Examples of imaging contrast agents include, for example, (a) contrast agents for use in connection with x-ray fluoroscopy, including metals, metal salts and oxides (particularly bismuth salts and oxides), and iodinated compounds, among others, (b) contrast agents for use in conjunction with ultrasound imaging, including inorganic and organic echogenic particles (i.e., particles that result in an increase in the reflected ultrasonic energy) or inorganic and organic echolucent particles (i.e., particles that result in a decrease in the reflected ultrasonic energy), and (c) contrast agents for use in conjunction with magnetic resonance imaging (MRI), including contrast agents that contain elements with relatively large magnetic moment such as Gd(III), Mn(II), Fe(III).

While the devices and methods of this disclosure have been described in terms of various preferred embodiments, it may be apparent to those of skill in the art that variations can be applied without departing from the concept, spirit and scope of the disclosure. All such similar substitutes and modifications apparent to those skilled in the art are deemed to be within the spirit, scope and concept of the disclosure as defined by the appended claims.

What is claimed is:

1. A radiofrequency ablation device comprising:
   a needle electrode configured to perform a radiofrequency ablation procedure;
   at least one anti-regeneration chemical agent that inhibits or prevents nerve regeneration; and
   a detachable sheath disposed over the needle electrode;
   wherein the detachable sheath releases the at least one anti-regeneration agent after detachment of the detachable sheath within a subject.

2. The radiofrequency ablation device of claim 1, wherein the detachable sheath is crumpled when detached from the needle electrode.

3. The radiofrequency ablation device of claim 1, wherein the at least one anti-regeneration chemical agent of the detachable sheath is one of: an anti-microtubule agent, an anti-neoplastic agent, a glial scar formation agent, an agent to induce the collapse or paralysis of neuronal growth cones, or a chemical agent that de-activates Schwann cells.

4. The radiofrequency ablation device of claim 3, wherein the at least one anti-regeneration chemical agent of the detachable sheath is one of: a taxol, vincristine, vindesine, vinorelbine, Nocodazole, Myelin-Associated Glycoprotein (MAG), or Semaphorin-3A.

5. The radiofrequency ablation device of claim 1, further comprising a lumen through which a vacuum source is configured to be applied to the detachable sheath.

6. The radiofrequency ablation device of claim 1, wherein the detachable sheath comprises a growth agent that causes an ablated nerve to grow into the detachable sheath.

7. The radiofrequency ablation device of claim 1, wherein the detachable sheath comprises a matrix material comprising one of a synthetic biostable polymer, a biodegradable polymer, a naturally occurring polymers, and a biologic.

8. The radiofrequency ablation device of claim 1, wherein the detachable sheath comprises a matrix material comprising one of a polyvinylidene fluoride (PVDF), poly(vinylidene fluoride-co-hexafluoropropene) (PVDF-HFP), poly(styrene-b-isobutylene-b-styrene) (SIBS), poly(lactide-co-glycolide) (PLG), polylactide(PLA), poly-D-lactide (PDLA), poly-L-lactide (PLLA), and poly-D,L-lactide (PDLLA).

9. A radiofrequency ablation device comprising:
a needle electrode configured to perform a radiofrequency ablation procedure;
a detachable sheath disposed over the needle electrode; and
at least one anti-regeneration chemical agent that inhibits or prevents nerve regeneration;
wherein a material of the detachable sheath comprises a growth agent that causes an ablated nerve to grow into the detachable sheath.

10. The radiofrequency ablation device of claim 9, wherein the anti-regeneration chemical agent is one of: an anti-microtubule agent, an anti-neoplastic agent, a glial scar formation agent, an agent to induce the collapse or paralysis of neuronal growth cones, or a chemical agent that de-activates Schwann cells.

11. The radiofrequency ablation device of claim 10, wherein the anti-regeneration chemical agent is one of: a taxol, vincristine, vindesine, vinorelbine, Nocodazole, Myelin-Associated Glycoprotein (MAG), or Semaphorin-3A.

* * * * *